United States Patent
Schneider et al.

(10) Patent No.: US 6,872,861 B2
(45) Date of Patent: Mar. 29, 2005

(54) PROCESS FOR PREPARING POLYFLUOROALKYLITHIUM COMPOUNDS

(75) Inventors: Marielouise Schneider, Leverkusen (DE); Albrecht Marhold, Leverkusen (DE); Alexander Kolomeitsev, Kiew (UA); Alexander Kadyrov, Moskau (RU); Gerd-Volker Röschenthaler, Bremen (DE); Jan Barten, Bremen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/165,259

(22) Filed: Jun. 7, 2002

(65) Prior Publication Data

US 2003/0065135 A1 Apr. 3, 2003

(30) Foreign Application Priority Data

Jun. 13, 2001 (DE) .......................... 101 28 703

(51) Int. Cl.⁷ .................. C07C 19/00; C07C 19/08; C07C 17/00; C07C 21/18
(52) U.S. Cl. ................. 570/140; 570/141; 570/142; 570/143; 570/144; 570/162; 570/175; 570/190; 528/488
(58) Field of Search ................. 570/140, 141, 570/142, 143, 144, 162, 175, 190; 528/488

(56) References Cited

U.S. PATENT DOCUMENTS 6,207,846 B1  3/2001  Barnes et al. ............... 556/447
2002/0022734 A1  2/2002  Marhold et al. ............ 556/415

OTHER PUBLICATIONS

Piettre, Serge,R. et al: "Easy and general access to .alpha., .alpha.–difluoromethylene phosphonothioic acids. A new class of compounds" Tetrahedron Letters (1996), 37(13), 2229–32 XP002211887 Seite 2230 Seite 2232; Beispiel 12.

Tetrahedron Letters, vol. 26, No. 43, pp 5243–5246, (month unavailable) 1985 Pentafluoroethyllithuim. Generation and Use in Synthesis by Paul G. Gassman and Neil J. O'Reilly.

J. Chem. Soc. (month unavailable) 1962, pp. 1993–1999 Organometallic and Metalloid Compounds Made from Heptafluoro–2–iodopropane, and their Properties by R. D. Chambers, W. K. R. Musgrave and J. Savory.

Adcock, James L. et al: "Synthesis and reactions of perfluoroneopentyllithium" J. Org. Chem. (1979), 44(19), 3431–3, XP002211886 das ganze dokument.

Primary Examiner—Elvis O. Price
(74) Attorney, Agent, or Firm—Diderico van Eyl; Godfried R. Akorli

(57) ABSTRACT

The invention relates to a process for preparing polyfluoroalkyl-lithium compounds by deprotonation of polyfluoroalkyl compounds by means of lithium bases.

10 Claims, No Drawings

PROCESS FOR PREPARING POLYFLUOROALKYLITHIUM COMPOUNDS

BACKGROUND OF THE INVENTION

The invention relates to a process for preparing polyfluoroalkyl-lithium compounds by deprotonation of polyfluoroalkyl compounds by means of lithium bases.

Organic compounds that are substituted by polyfluoroalkyl groups are becoming increasingly important, for example, in the development of new active compounds, since such substituents are inert under physiological conditions and allow fine control of, for example, the lipophilicity and the reactivity of the basic organic skeleton.

The introduction of polyfluoroalkyl substituents into an organic molecule is frequently carried out using polyfluoroalkyl-metal compounds that can undergo the addition and substitution reactions typical of nucleophilic reagents.

Thus, for example, the synthesis of pentafluoroethyltrimethylsilane, a reagent for the preparation of pentafluoroethylated products, can be carried out by reaction of pentafluoroethyllithium (for the preparation of which, see, for example, P. G. Gassmann and N. J. O'Reilly, Tetrahedron 1985, 26, page 5243) with trimethylchlorosilane according to equation (a).

$$CF_3CF_2Li + (CH_3)_3SiCl \rightarrow (CH_3)_3SiCF_2CF_3 + LiCl \qquad (a)$$

In addition, such organometallic compounds react with aldehydes, as shown in equation (b), to form polyfluoroalkyl-substituted alcohols that are valuable starting materials for the production of materials for liquid crystal displays (LCDs) and are therefore of industrial interest.

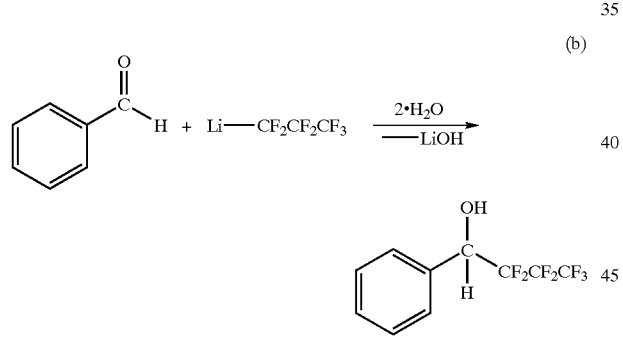

(b)

The polyfluoroalkyl compounds of the metals magnesium and zinc have also been examined (R. D. Chambers, W. K. R. Musgrave, and J. Savory, J. Chem. Soc., 1962, pages 1993–1999). However, compared with their lithium analogs, these compounds display only unsatisfactory reactivity, so that they do not come into question for industrial use.

In the past, polyfluoroalkyllithium compounds ($R^F$—Li) have been obtained exclusively by means of metal-halogen exchange reactions according to equation (c), with the replaceable halogens of the starting compounds being able to be chlorine, bromine or iodine.

$$R-Li + R^F-Hal \rightarrow R-Hal + R^F-Li \qquad (c)$$

Recently, however, chlorofluorocarbons (CFCs) in particular have been the subject of replacement measures because of the damage they cause to the ozone layer. The likewise ozone-depleting bromine and iodine homologs have the additional disadvantage that they are not only very expensive but, due to their high molar mass, their use results in formation of large amounts of waste products for which correct disposal represents an additional problem.

There is therefore a need to prepare the synthetic valuable poly-fluoroalkyllithium compounds without use of mixed halofluorocarbons.

It has now been found that polyfluoroalkyl compounds can be deprotonated by means of lithium bases.

SUMMARY OF THE INVENTION

The invention accordingly provides a process for preparing poly-fluoroalkyllithium compounds comprising deprotonating polyfluoroalkyl compounds by means of lithium bases.

DETAILED DESCRIPTION OF THE INVENTION

Polyfluoroalkyl compounds used as starting materials in the process of the invention can be, for example, compounds containing polyfluoroalkyl radicals and having the general formula (I),

$$HCF_2R^1 \qquad (I)$$

where
$R^1$ is fluorine, $(CF_2)_nCF_3$, $(CF_2)_nR^2$,
n is an integer from 0 to 17, and
$R^2$ is tri($C_1$–$C_6$-alkyl)silyl, triphenylsilyl, cyclic alkyl having from 3 to 8 carbon atoms, straight-chain or branched alkyl having from 1 to 24 carbon atoms, aryl having from 6 to 10 carbon atoms, arylalkyl having from 7 to 18 carbon atoms, straight-chain or branched alkenyl having from 2 to 12 carbon atoms, straight-chain or branched alkoxy having from 1 to 12 carbon atoms, aryloxy having from 6 to 10 carbon atoms, heteroaryl having from 4 to 9 carbon atoms, heteroarylalkyl having from 5 to 17 carbon atoms, or heteroaryloxy having from 4 to 9 carbon atoms, where the heteroaryl radicals can each contain up to 2 hetero atoms selected from the group consisting of oxygen, sulfur, and nitrogen.

In the above-mentioned alkyl compounds, the alkyl radicals may, if desired, be substituted further by fluorine, di($C_1$–$C_6$-alkyl)amino, or alkylthio or alkyloxy each having from 1 to 12 carbon atoms.

The above-mentioned aromatic substituents may, if desired, bear up to 3 further substituents that can be selected independently from the group consisting of fluorine, cyclic alkyl having from 3 to 6 carbon atoms, straight-chain or branched alkyl having from 1 to 12 carbon atoms, straight-chain or branched alkoxy and alkylthio each having from 1 to 12 carbon atoms, straight-chain or branched alkenyl having from 2 to 12 carbon atoms, and di($C_1$–$C_6$-alkyl)amino, where the alkyl radicals may also form a ring.

In the process of the invention, preference is given to compounds of the general formula (I) in which
$R^1$ is fluorine, $(CF_2)_nCF_3$, $(CF_2)_nR^2$,
n is an integer from 0 to 17, and
$R^2$ is tri($C_1$–$C_6$-alkyl)silyl, straight-chain or cyclic, unbranched or branched alkyl having from 1 to 12 carbon atoms, phenyl, phenyl-alkyl having from 7 to 18 carbon atoms, straight-chain alkoxy having from 1 to 12 carbon atoms, phenyloxy, heteroaryl having 4 or 5 carbon atoms, heteroarylalkyl having from 5 to 17 carbon atoms, or heteroaryloxy having from 4 to 9 carbon atoms, where the heteroaryl radicals can each contain a hetero atom selected from the group consisting of oxygen, sulfur, and nitrogen.

In the above-mentioned alkyl compounds, the alkyl radicals may, if desired, be further substituted by fluorine, di($C_1$–$C_6$-alkyl)amino, or alkylthio or alkyloxy each having from 1 to 6 carbon atoms.

The above-mentioned aromatic substituents may, if desired, bear up to three further substituents that can be selected independently from the group consisting of fluorine, straight-chain alkyl having from 1 to 6 carbon atoms, straight-chain alkoxy or alkylthio each having from 1 to 6 carbon atoms, or di($C_1$–$C_6$-alkyl)amino, where the alkyl radicals may also form a ring.

In the process of the invention, particular preference is given to compounds of the general formula (I) in which $R^1$ is fluorine, $(CF_2)_nCF_3$, $(CF_2)_nR^2$, n is an integer from 1 to 11, and $R^2$ is phenyloxy that may, if desired, be further substituted by alkyloxy having from 1 to 6 carbon atoms.

The respective polyfluoroalkyl compounds can, for example, be initially charged in a solvent which is inert towards organolithium compounds.

Such solvents can, for example, be cyclic or acyclic ethers such as 1,4-dioxane, tetrahydrofuran, tetrahydropyran, diethyl ether, methyl tert-butyl ether, di-n-butyl ether, ethylene glycol dimethyl ether (glyme), or diethylene glycol dimethyl ether (diglyme), branched or straight-chain alkanes or cycloalkanes such as n-pentane, n-hexane, cyclohexane, methylcyclohexane, n-heptane, n-octane, or fractions obtained by distillation of petroleum (petroleum ether). The solvents can, for example, be used individually or in admixture.

Preference is given to diethyl ether, tetrahydrofuran, n-pentane, and n-hexane or mixtures of these solvents.

Polyfluoroalkyl compounds that are gaseous at room temperature can be added to the solvent by condensation into the solvent or after prior liquefaction by cooling. Preference is given to condensation into the cooled solvent or the solvent mixture.

The deprotonation can be carried out using reagents that contain the organolithium compounds and, if desired, complexing compounds and, if desired, activating additives.

Lithium bases that can be used are, for example, organolithium compounds such as phenyllithium; compounds of the general formula (II)

$LiCR^3R^4R^5$            (II)

where, independently of one another, $R^3$ is hydrogen, methyl, ethyl, n-propyl, isopropyl, n-butyl, isobutyl, tert-butyl, n-pentyl, n-hexyl, or n-heptyl, $R^4$ is hydrogen or methyl, and $R^5$ is hydrogen or methyl, or $CR^4R^5R^6$ is cyclopentyl or cyclohexyl; or lithium amides such as lithium bis(trimethylsilyl)amide or lithium diisopropylamide (LDA).

Preference is given to n-butyllithium, sec-butyllithium, tert-butyl-lithium, phenyllithium, lithium-bis(trimethylsilyl) amide, and lithium diiso-propylamide.

The lithium bases are preferably used as a solution in, for example, the above-mentioned solvents.

Particular preference is given to the commercially available solutions of n-butyllithium in n-hexane, sec-butyllithium in cyclohexane, tert-butyllithium in pentane, and phenyllithium in cyclohexane/diethyl ether.

Suitable complexing compounds are complexing agents that are inert towards lithium bases, for example, crown ethers such as 12-crown-4 or dibenzo-12-crown-4, cryptands such as cryptand[2.2.2], podands such as polyglycol ether, and amines such as N,N,N,N-tetramethylethylene-diamine (TMEDA).

Possible activating reagents are, for example, compounds that form superbasic mixtures with lithium bases, for example, sodium tert-butoxide or potassium tert-butoxide.

The reaction temperature for the deprotonation step can be, for example, from –110 to –50° C., preferably from –80 to –60° C.

The deprotonation can be carried out, for example, by adding the lithium base or preferably a solution thereof to the polyfluoroalkyl compound or preferably a solution thereof. The reverse order of addition or simultaneous addition to a solvent that has been cooled to the reaction temperature are also possible. The lithium base and the polyfluoroalkyl compound can also be added continuously to one another or the reaction can be carried out in a flow-through microreactor.

Very particular preference is given to adding a solution of the lithium base to a solution of the polyfluoroalkyl compound.

The ratio of lithium base to polyfluoroalkyl compound can be, for example, from 0.05 to 1.3, preferably from 0.5 to 1.0.

Complexing compounds can, for example, be used in a ratio of from 0.1 to 1.2 (preferably from 0.8 to 1.1), based on the lithium base used.

Activating reagents can, for example, be used in a ratio of from 0.1 to 2.0 (preferably from 0.9 to 1.1), based on the lithium base used.

The sum of addition time and after-stirring time can be, for example, from 5 minutes to 24 hours, preferably from 30 minutes to 4 hours.

The polyfluoroalkyllithium compounds prepared according to the invention can, for example, be stored in solution or can immediately be reacted further in solution.

Due to the fact that the compounds slowly decompose above –50° C., preference is given to the direct further reaction of the reaction solutions.

The process of the invention for preparing polyfluoroalkyllithium compounds is particularly suitable for integration into a process for preparing further-substituted polyfluoroalkyl compounds. This process comprises the following steps:

(a) Preparation of polyfluoroalkyllithium compounds by the process of the invention, and (b) Reaction of the polyfluoroalkyllithium compounds with electrophiles.

Step (b) can, for example, be carried out by customary methods using electrophiles such as the following:

(1) silanes of the general formula (III)

$HalSiR^6R^7R^8$            (III), where

Hal can be chlorine, bromine or iodine and, independently thereof, $R^6$, $R^7$, and $R^8$ can, independently of one another, each be hydrogen, fluorine, methyl, n-ethyl, n-propyl, n-butyl, n-hexyl, phenyl, p-tolyl, benzyl, trifluoromethyl, or perfluoroalkyl having from 2 to 12 carbon atoms, (2) halophosphines such as diphenylchlorophosphine, dichlorophenyl-phosphine, or bis(dichlorophosphino) ethane, (3) aromatic or aliphatic aldehydes such as acetaldehyde, benzaldehyde, p-methylbenzaldehyde, or p-anisaldehyde, (4) halogens such as chlorine, bromine, or iodine, (5) interhalogens such as ICl, (6) ketones such as acetone, ethyl methyl ketone, or acetophenone, (7) alkyl or arylalkyl bromides, iodides, mesylates, p-tosylates, or trifluoromethanesulfonates, or (8) further electrophiles such as carbon dioxide, carbon disulfide ($CS_2$), thionyl chloride, or carbodiimides.

Preferred electrophiles for step (b) are trimethylchlorosilane and aromatic aldehydes.

The particular advantages of the process of the invention are the high total yields of substituted polyfluoroalkyl compounds, the comparatively environmentally friendly and inexpensive starting compounds, and the minimization of waste products compared with the processes known hitherto.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1
Preparation of Pentafluoroethyltrimethylsilane from Pentafluoroethane and Trimethylchlorosilane 50 ml of diethyl ether were placed in a 4-neck flask fitted with anchor stirrer, dropping funnel, and internal thermometer and, at −80° C., 3.6 g (30 mmol) of pentafluoroethane were condensed in via a gas inlet tube, after which 9.1 g (20 mmol) of n-butyllithium as a 15% strength solution in n-hexane were slowly added dropwise. The temperature during this addition was not allowed to exceed −70° C. The mixture was stirred for another 30 minutes at an internal temperature of from −60° C. to −65° C. and 2.2 g (20 mmol) of trimethylchlorosilane in 10 ml of diethyl ether were then slowly added dropwise. The cooling was removed, the mixture was allowed to come to room temperature, and the desired product penta-fluoroethyltrimethylsilane was purified by distillation. The yield was 93% of theory.

Example 2
Preparation of (2-[3-methoxyphenoxyl]-1,1,2,2-tetrafluoroethyl)trimethyl-silane from 2-(3-methoxyphenoxy)-1,1,2,2-tetrafluoroethane and trimethylchlorosilane.

6.7 g (30 mmol) of 2-(3-methoxyphenoxy)-1,1,2,2-tetrafluoroethane were placed in a 4-neck flask fitted with anchor stirrer, dropping funnel, and internal thermometer at −78° C. and 9.1 g (20 mmol) of n-butyllithium as a 15% strength solution in n-hexane were then slowly added dropwise. The mixture was stirred for another 30 minutes at an internal temperature of not more than −60° C. and 2.2 g (20 mmol) of trimethylchlorosilane in 10 ml of diethyl ether were then slowly added dropwise. The reaction mixture was stirred for another 3 hours at from −70 to −80° C. and was subsequently allowed to warm to room temperature. The solvent was removed, the residue was taken up in pentane, and the LiCl was filtered off. The desired product (2-[3-methoxyphenoxyl]-1,1,2,2-tetrafluoroethyl)trimethylsilane was purified by distillation. The yield was 75% of theory.

Example 3
Preparation of heptafluoropropylphenyl alcohol from 1H-heptafluoro-propane and benzaldehyde 60 ml of ether and 3.6 g (30 mmol) of 1H-heptafluoropropane were placed in a 4-neck flask fitted with anchor stirrer, dropping funnel, and internal thermometer and the mixture was cooled to −80° C. 9 g (20 mmol) of tert-BuLi as a 15% strength solution in pentane were then added dropwise and the mixture was stirred for another 30 minutes at this temperature. 2.1 g (20 mmol) of benzaldehyde in 10 ml of ether were subsequently added dropwise. After stirring at −80° C. for 2 hours, the yellow solution was allowed to come to room temperature and dilute hydrochloric acid was added. The mixture was extracted three times with ether and the combined organic phases were dried and filtered. Purification by distillation gave heptafluoropropylphenyl alcohol in a yield of 70%.

What is claimed is:

1. A process for preparing polyfluoroalkyllithium compounds comprising deprotonating polyfluoroalkyl compounds of the formula (I)

$$HCF_2R^1 \tag{I}$$

wherein $R^1$ is fluorine, $(CF_2)_nCF_3$, $(CF_2)_nR^2$, n is an Integer from 0 to 17, and $R^2$ is tri($C_1$–$C_6$-alkyl)silyl, triphenylsilyl, cyclic alkyl having from 3 to 8 carbon atoms, straight-chain or branched alkyl having from 1 to 24 carbon atoms, aryl having from 6 to 10 carbon atoms, arylalkyl having from 7 to 18 carbon atoms, straight-chain or branched alkenyl having from 2 to 12 carbon atoms, straight-chain or branched alkoxy having from 1 to 12 carbon atoms, aryloxy having from 6 to 10 carbon atoms, heteroaryl having from 4 to 9 carbon atoms, heteroarylalkyl having from 5 to 17 carbon atoms, heteroaryloxy having from 4 to 9 carbon atoms, where (i) the heteroaryl radicals each contain up to 2 hetero atoms selected from the group consisting of oxygen, sulfur, and nitrogen, (ii) the alkyl radicals are optionally substituted further by fluorine, di($C_1$–$C_6$-alkyl)amino, or alkylthio or alkyloxy each having from 1 to 12 carbon atoms, and (iii) the aromatic substituents optionally bear 1, 2, or 3 further substituents selected independently from the group consisting of fluorine, cyclic alkyl having from 3 to 6 carbon atoms, straight-chain or branched alkyl having from 1 to 12 carbon atoms, straight-chain or branched alkoxy or alkylthio each having from 1 to 12 carbon atoms, straight-chain or branched alkenyl having from 2 to 12 carbon atoms, di($C_1$–$C_6$-alkyl)amino, or N—($C_5$–$C_{12}$)-azacycloalkyl;

wherein the deprotonation is carried out with a lithium base.

2. The process according to claim 1 wherein the polyfluoroalkyl compounds are compounds of the formula (I)

$$HCF_2R^1 \tag{I}$$

wherein $R^1$ is fluorine, $(CF_2)_nCF_3$, $(CF_2)_nR^2$, n is an integer from 0 to 17, and $R^2$ is phenyloxy or phenoxy substituted by 1, 2, or 3 alkyloxy groups having from 1 to 6 carbon atoms.

3. The process according to claim 1 wherein the lithium base is lithium bis(trimethylsilyl)amide, lithium diisopropylamide, phenyllithium, or a compound of the formula (II)

$$LiCR^3R^4R^5 \tag{II}$$

where, independently of one another, $R^3$ is hydrogen, methyl, ethyl, n-propyl, isopropyl, n-butyl, isobutyl, tert-butyl, n-pentyl, n-hexyl, or n-heptyl, $R^4$ is hydrogen or methyl, and $R^5$ is hydrogen or methyl, or $CR^4R^5R^6$ is cyclopentyl or cyclohexyl.

4. The process according to claim 2 wherein the lithium base is n-butyllithium, sec-butyllithium, tert-butyllithium, or phenyllithium.

5. The process according to claim 1 wherein the lithium base is used as a solution.

6. The process according to claim 1 wherein deprotonation is carried out at from −110 to −50° C.

7. The process according to claim 1 wherein deprotonation is carried out in the presence of one or more complexing compounds.

8. The process according to claim 7 wherein deprotonation is carried out in the presence of a crown ether, a cryptand, a podand, a polyether, or an amine or a combination thereof.

9. The process according to claim 1 wherein deprotonation is carried out in the presence of potassium tert-butoxide or sodium tert-butoxide.

10. A process for preparing a polyfluoroalkyl compound comprising
  (a) deprotonating a polyfluoroalkyl compound according to claim 1, and
  (b) reacting the deprotonated polyfluoroalkyl compound with an electrophile.

* * * * *